US008338370B2

(12) United States Patent (10) Patent No.: US 8,338,370 B2
Ricardo et al. (45) Date of Patent: *Dec. 25, 2012

(54) METHODS AND COMPOSITIONS FOR PROMOTING ORGAN DEVELOPMENT

(75) Inventors: Sharon Denise Ricardo, Mornington (AU); David Arthur Hume, Roslin (GB); Melissa Helen Little, Brisbane (AU); Christina Victoria Jones, Wheelers Hill (AU)

(73) Assignee: Kintan Pty Ltd., South Yarra (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/236,177

(22) Filed: Sep. 19, 2011

(65) Prior Publication Data

US 2012/0009139 A1 Jan. 12, 2012

Related U.S. Application Data

(63) Continuation of application No. 11/902,062, filed on Sep. 18, 2007, now abandoned, which is a continuation-in-part of application No. PCT/AU2007/001372, filed on Sep. 17, 2007, which is a continuation-in-part of application No. PCT/AU2006/000357, filed on Mar. 17, 2006.

(30) Foreign Application Priority Data

Mar. 18, 2005 (AU) .............................. 2005901346
Sep. 15, 2006 (AU) .............................. 2006905099
Sep. 18, 2006 (AU) .............................. 2006905156

(51) Int. Cl.
*A61K 38/00* (2006.01)
*C07K 14/475* (2006.01)
*A61P 13/12* (2006.01)

(52) U.S. Cl. ........................ 514/7.6; 514/15.4; 530/300

(58) Field of Classification Search ........................ None
See application file for complete search history.

(56) References Cited

U.S. PATENT DOCUMENTS 5,422,105 A * 6/1995 Ralph et al. .................. 424/85.1
5,556,620 A 9/1996 Ralph et al.

OTHER PUBLICATIONS

Stoll et al., JAMA 292: 2357-2365, 2004.*
Lin et al., J. Mammary Gland Biol. and Neopl. 7:147-162, 2002.*
Bhatnagar et al., Dev. 121: 1333-1339, 1995.*
Michaelson et al., Dev. 122: 2661-2672, 1996.*
Bertram, John F.; "Analyzing Renal Glomeruli with the New Stereology"; Dept. of Anatomy and Cell Biology, University of Melbourne, Parkville, Victoria 3052, AU; 110-165.
Dressler, Gregory R.; "Development of the Excretory System"; Department of Pathology, University of Michigan, Ann Arbor, Michigan 48109 (2002) Chapter 18; 395-420.
Rossant, Janet et al.; "Emerging Asymmetry and Embryonic Patterning in Early Mouse Development"; *Developmental Cell*; 7 (Aug. 2004) 155-164.
Hayashi, Masatoshi et al.; "Elevation of Amniotic Fluid Macrophage Colony-Stimulating Factor in Normotensive Pregnancies That Delivered Small-For-Gestational-Age Infants"; *American Journal of Reproductive Immunology*; 57 (2007) 488-494.
Hinchliffe, S. A. et al.; "Human Intrauterine Renal Growth Expressed in Absolute Number of Glomeruli Assessed by the Disector Method and Cavalieri Principle"; *Laboratory Investigation*; 64:6 (1991) 777-784.
Horster, Michael F. et al.; "Embryonic Renal Epithelia: Induction, Nephrogenesis and Cell Differentation"; *Physiological Reviews*; 79:4 (Oct. 1999) 1157(3).
Hume, David A. et al.; "Detection of *c-fms* Protooncogene in Early Mouse Embryos by Whole Mount in situ Hybridization Indicates Roles for Macrophages in Tissue Remodelling"; *British Journal of Haematology*, 90 (1995) 939-942.
Kett, Michelle M. et al.; "Glomerular Dimensions in Spontaneously Hypertensive Rats: Effects of $AT_1$ Antagonism"; *Journal of Hypertension*; 14:1 (1996) 107-113.
Keith Jr., James C. et al.; "Maternal Serum Levels of Macrophage Colony-Stimulating Factor Are Associated With Adverse Pregnancy Outcome"; *European Journal of Obstetrics & Gynecology and Reproductive Biology*; 89 (2000) 19-25.
Dai, Xu-Ming et al.; "Targeted Disruption of the Mouse Colony-Stimulating Factor 1 Receptor Gene Results in Osteopetrosis, Mononuclear Phagocyte Deficiency, Increased Primitive Progenitor Cell Frequencies, and Reproductive Defects"; *Blood*; 99:1 (2002) 111-120.
Seckl, Jonathan R. et al.; "Mechanisms of Disease: Glucocorticoids, Their Placental Metabolism and Fetal 'Programming' of Adult Pathophysiology"; *Nature Clinical Practice, Endocrinology & Metabolism*; 3:6 (2007) 479-488.
Rae, Fiona et al.; "Characterisation and Trophic Functions of Murine Embryonic Macrophages Based Upon the Use of a *Csf1r*-EGFP Transgene Reporter"; *Developmental Biology*; 308 (2007) 232-246.
Pandit, Jayvardhan et al.; "Three-Dimensional Structure of Dimeric Human Recombinant Macrophage Colony-Stimulating Factor"; *Science*; 258:5086 (Nov. 20, 1992) 1358-1362.
Schinckel, A. P. et al.; "Analysis of Pig Growth From Birth to Sixty Days of Age"; (2003); Swine Research Report, Purdue University; pp. 57-67.
Knižetová, H. et al.; "Comparative Study of Growth Curves in Poultry"; Genetics Selection Evolution; (1995) 27, 365-375.
Gardner, D. S. et al.; "Factors Affecting Birth Weight in Sheep: Maternal Environment"; Reproduction; (2007); 133; 297-307.

(Continued)

*Primary Examiner* — Gyan Chandra
(74) *Attorney, Agent, or Firm* — Jones Day

(57) ABSTRACT

Compositions and methods are provided for promoting organ development in warm blooded animals, and in particular in certain aspects a premature infant or foetus. Compositions and methods are also provided for the administration of at least one colony stimulating factor-1 protein (CSF-1), precursor, variant, analogue, derivative thereof, or combinations thereof, or otherwise, at least one nucleic acid molecule encoding colony stimulating factor-1 protein (CSF-1), precursor, variant, analogue, derivative thereof, or combinations thereof.

20 Claims, 3 Drawing Sheets

OTHER PUBLICATIONS

Elliot, C. et al.; "Factors Affecting Foal Birth Weight in Thoroughbred Horses"; Theriogenology; 71 (2009) 683-689.

Draper, Elizabeth S. et al.; "Prediction of Survival for Preterm Births by Weight and Gestational Age: Retrospective Population Based Study"; British Medical Journal; vol. 319; Oct. 23, 1999; pp. 1093-1097.

Mickle et al., Med. Clin. North Am., vol. 84(3), p. 597-607, 2000.

Millipore_GF053, product sheet, one page, printed by the Examiner on Jun. 20, 2011.

Google search for Millipore catalog No. GF053 CSF-1, one page, available from Google search results and printed on Jun. 20, 2011.

* cited by examiner

METHODS AND COMPOSITIONS FOR PROMOTING ORGAN DEVELOPMENT

CROSS-REFERENCE TO RELATED APPLICATIONS

This application is a continuation of U.S. application Ser. No. 11/902,062 filed Sep. 18, 2007, which is a continuation-in-part of a PCT application filed in the Australian Receiving Office on Sep. 17, 2007, (which claims priority to Australian Provisional Application No. AU2006905099, filed on 15 Sep. 2006, entitled "Method For Promoting Organ Development" and Australian Provisional Application No. AU 2006905156, filed 18 Sep. 2006, entitled "Method For Promoting Organ Development"), and is also a continuation-in-part of International Patent Application No. PCT/AU2006/000357, filed Mar. 17, 2006, entitled "Renal Repair and Regeneration" (which claims priority to Australian Provisional Application No. AU2005901346, filed 18 Mar. 2005, entitled "Renal Repair and Regeneration"). Each of these documents, including those in parenthesis, are incorporated herein by reference in their entirety. In addition, each of the following documents are incorporated herein by reference in its entirety:

Bertram J F (1995) Analyzing renal glomeruli with the new stereology; International Review of Cytology; 161: 111-172.

Dressler, G. R. (2002). Development of the Excretory System. *Mouse Development—Patterning, Morphogenesis and Organogenesis.*

J. Rossant and P. P. L. Tam. Houston, Academic Press: 395; Goldenring J (2004). Respiratory Distress Syndrome in Infants. MedlinePlus Medical Encyclopedia. [Available at http://www.nlm.nih.gov/medlineplus/ency/article/001563.htm].

Hayashi M. Zhu K. Sagesaka T. Fukasawa I. Inaba N. Elevation of amniotic fluid macrophage colony-stimulating factor in normotensive pregnancies that delivered small-for-gestational-age infants. American Journal of Reproductive Immunology. 57(6):488-94, 2007 June Hinchliffe, S., Sargent, P., et al. (1991). "The effect of intrauterine growth expressed in absolute number of glomeruli assessed by the "disector" method and Cavalieri principle." *Lab Investigator* 64: 777-784.

Horster, M., Braun, G., et al. (1999). "Embryonic renal epithelia: Induction, nephrogenesis and cell differentiation." *Physiological Reviews* 79(4): 1157-1191.

Hume, D., Monkley, S., et al. (1995). "Detection of c-fms protooncogene in early mouse embryos by whole mount in situ hybridisation indicates roles for macrophages in tissue remodelling." British Journal of Haematology 90(4): 939-942.

Kett M M, Alcorn D, Bertram J F, Anderson W P (1996). Glomerular dimensions in spontaneously hypertensive rats: effects of AT1 antagonism. Journal of Hypertension; 14: 107-113.

Keith J C Jr. Pijnenborg R. Luyten C. Spitz B. Schaub R. Van Assche F A. Maternal serum levels of macrophage colony-stimulating factor are associated with adverse pregnancy outcome. European Journal of Obstetrics, Gynecology, & Reproductive Biology. 89(1):19-25, 2000.

Wei S. Lightwood D. Ladyman H. Cross S, Neale H. Griffiths M. Adams R. Marshall D. Lawson A. McKnight A J. Stanley E R. Modulation of CSF-1-regulated post-natal development with anti-CSF-1 antibody. Immunobiology. 210(2-4):109-19, 2005.

Dai X M. Zong X H. Sylvestre V. Stanley E R. Incomplete restoration of colony-stimulating factor 1 (CSF-1) function in CSF-1-deficient Csf1op/Csf1op mice by transgenic expression of cell surface CSF-1. Blood. 103(3):1114-23, 2004.

Seckl J R, Holmes M C. Mechanisms of disease: glucocorticoids, their placental metabolism and fetal 'programming' of adult pathophysiology. Nat Clin Pract Endocrinol Metab. 3(6):479-88, 2007.

Gennaro, Alfonso, *Remington's Pharmaceutical Sciences,* 18th edition, Mack Publishing Co. (1990).

University of the Sciences in Philadelphia (editor) *Remington: The Science and Practice of Pharmacy* 21st edition (2005).

Rae F, Woods K, Sasmono T, Campanale N, Taylor D, Ovchinnikov D, Grimmond S M, Hume D A, Ricardo S D, and Little M H. Characterisation and trophic functions of murine embryonic macrophages based upon the use of a CSF-IR-EGFP transgenic reporter. Developmental Biology (In Press, accepted May 24) 2007.

FIELD OF THE INVENTION

The present disclosure relates to embodiments for promoting organ development in warm blooded animals, and in particular in certain aspects a premature infant or foetus. Compositions and methods are provided for the administration of colony stimulating factor-1 protein (CSF-1), or a precursor, variant, analogue or derivative thereof, or otherwise, a nucleic acid molecule encoding colony stimulating factor-1 protein (CSF-1), or a precursor, variant, analogue or derivative thereof.

BACKGROUND OF THE INVENTION

Compared to infants who have born following a normal, full term pregnancy, premature infants, particularly babies born before 32 weeks of gestation, are at a considerably greater risk of developing a number of serious health problems including, for example, renal and lung disorders.

For instance, the low birth weight and insufficient physical development of premature infants predisposes them to respiratory complications such as respiratory distress syndrome (RDS) and chronic lung disease (also known as bronchopulmonary dysplasia). RDS is associated with irregular breathing difficulties and occurs in approximately 60 to 80 percent of infants born before 28 weeks gestation, and in 15 to 30 percent of those born between 32 and 36 weeks of gestation. Treatment of such infants typically involves supplemental oxygen, but in some cases, also requires the use of a mechanical ventilator and continuous positive airway pressure. Moreover, in severe cases, treatment will additionally involve the administration of an artificial lung surfactant. While such treatments are very successful, long-term ventilator treatment is undesirable since this can lead to lung deterioration, which in turn, can lead to bronchopulmonary dysplasia.

It is also known that premature infants are born with reduced numbers of nephrons (filtration units of the kidney), an outcome that may be associated with increased risk of developing hypertension and reduced renal function following injury later in life.

Lung Development: Analogies Between Human and Mouse

The human lung is derived from the foregut at about 4 weeks gestation and begins as a diverticulum. The lung diverticulum is covered with splancnic mesoderm that gives rise to the tissue components of the mature adult lung such as cartilage, smooth muscle and blood vessels. Lung development is characterised by branching morphogenesis that gives rise to the primary, secondary and tertiary bronchi. The stages of foetal lung development are classified into three distinct phases, namely; the pseudoglandular, canalicular and saccular phases. Some aspects of alveolar lung development including epithelial cell differentiation begin in the canalicular phase. However, approximately 15-18% of alveoli form late in gestation, with most of the alveoli formed after birth. Shortly after birth, the surface area of the air-blood interface increases with the formation of the alveolar ducts and sacs.

Premature infants can survive with lung development in the late canalicular or early saccular phase. This is a phase when the conducting airways have stopped branching and are enlarging at their distal termini. There is a progressive loss of extracellular matrix and mesenchymal cells that separate the capillaries from the sites of alveoli. These premature infants survive without alveoli by treatment involving mechanical ventilation and the administration of an artificial lung surfactant, although, as mentioned above, they are at risk of developing bronchopulmonary dysplasia.

In mice, the lung also arises from the ventral foregut, but at approximately embryonic day 9.5 (E9.5). Subsequently, the respiratory tree develops through the pseudoglandular (E9.5-16.5), canalicular (E16.5-17.5), and saccular (E17.5-postnatal day 5) phase. While mouse and human lung development is highly analogous from an embryological point of view and while the same genes are critical in both organisms, in contrast to the human lung, alveolarisation is not complete before birth in the mouse. At birth, the mouse lungs consists of immature terminal saccules with some secondary septa, with alveolarisation and alveolar separation occurring during the during the first 1-3 postnatal weeks. The alveolar surfaces increase through the enlargement of pre-existing alveoli with formation of new alveoli.

Kidney Development: Analogies Between Humans and Mice

The development of the kidney is highly analogous between human and mouse with respect to the embryological origin of the tissues involved, the morphogenetic processes and the genes regulating these processes.

In the human (as for the mouse), both the renal and genital systems originate from the intermediate mesoderm. Development of the kidney undergoes three distinct stages before resulting in the mature adult kidney. The process begins with the formation of the pronephros, then the mesonephros and finally the metanephros, after which the pronephros and mesonephros regress, and the metanephros remains to form the functional adult kidney. Metanephric development begins with the outgrowth of ureteric bud, originating from the Wollfian duct, invading the surrounding metanephric mesenchyme. The functional units within the kidney responsible for filtration of the blood, concentration of the filtrate to form urine and reclamation of water and ions are the nephrons. The formation of these functional units is referred to as nephrogenesis. Human nephrogenesis (development of kidney nephrons) is completed before birth. The number of nephrons in normal human kidneys ranges from approximately 300,000 to more than one million. After birth, the nephron number is complete and no new nephrons are able to be formed. In humans, development of the permanent kidney begins around gestational week 5. In the third trimester, 60% of nephrons are formed and continue to form until approximately 36 weeks. No new nephrons are formed after this time.

In the mouse (as with humans), there are three embryonic kidneys, the pronephros, mesonephros and metanephros, and the development of the final permanent kidney, the metanephros, begins with the outgrowth of ureteric bud, originating from the Wollfian duct, invading the surrounding metanephric mesenchyme. This occurs at around embryonic day 9-10.5 (E9-10.5) and requires inductive signals from the metanephric mesenchyme to initiate bud development. The induced mesenchyme sends reciprocal signals to induce growth and branching of the ureteric bud. Nephron formation (nephrogenesis) is induced when factors secreted by the ureteric bud cause the induction, condensation and aggregation of the mesenchyme. Each aggregate undergoes epithelialisation and then proceeds through the developmental stages of the polarised vesicle stage, the comma and the S-stage. There is continued branching with new aggregates forming at the tips, and this process continues with the induction of new nephrons. By the end of nephrogenesis, there are more than 26 terminally differentiated cell types with distinct location, morphology and function. Unlike the human, in the mouse kidney development continues in mice until around 7-10 days after birth.

Growth Factors in Kidney and Lung Development

Growth factors, aside from their influence in cell growth, contribute greatly to many processes including cell migration, morphogenesis, differentiation and proliferation. The roles of growth factors in branching morphogenesis in the lung and nephrogenesis in the kidney are controlled by an array of inductive and inhibitory signals. The crucial roles of factors including insulin-like growth factor-I and II (IGF-I and IGF-II), hepatocyte growth factor (HGF), and epithelial growth factor (EGF) have been well established in the developing lung and kidney. It is, however, considered that there may be numerous other growth factors which play significant roles in development of the lung and kidney.

In has been found that in warm blooded animals, using the embodiments disclosed it is possible to promote organ development (as reflected in, for some organs, an increase in organ weight), and more particularly, increased growth and/or enhanced nephrogenesis and lung maturation. It has also been found that promoting organ development and/or maturation in a warm blooded premature infant or foetus is possible.

SUMMARY OF THE INVENTION

Certain embodiments disclosed provide compositions for and methods for treating complications arising from or related to low birth weight in mammals, including for example, humans, pigs, horses, dogs and other livestock. Low birth weight may be caused by premature or preterm birth or by poor foetal growth, such as intrauterine growth restriction. There are many causes of poor foetal growth, some of which include chromosomal abnormalities, placental dysfunction, placenta previa, smoking, drug or alcohol abuse, amnionitis, abruptio placentae or preeclampsia, maternal hypertension, maternal hypoxemia, maternal toxemia, polyhydramnios, urinary tract infection, malnutrion, infection, anemia, diabetes, inadequate maternal weight gain and various diseases. The compositions and methods described herein may be used to treat and/or prevent any of these causes of low birth weight and the complications. In some embodiments, the compositions and methods described herein may be used specifically to treat or prevent causes of low birth weight such as foetal alcohol syndrome, placental insufficiency, intrauterine growth retardation (IUGD), foetal growth restriction as a result of infections, genetic abnormalities such as mutations in the gene that encodes 11-β-hydroxysteroid dehydrogenase type 2, maternal hypertension, diabetes, alcohol and illicit drug abuse or inadequate maternal weight gain.

Low birth weight in babies can result in a large number of complications including immature organ growth, such as immature lungs and kidneys, respiratory distress syndrome (RDS), intraventricular hemorrhage (IVH), Patent ductus arteriosus (PDA), necrotizing enterocolitis (NEC), retinopathy of prematurity (ROP), and osteopenia. The long term adverse effects of a low birth weight include increased risk of heart disease and renal failure, increased risk of diabetes and obesity and a possible consequence on intelligence. The compositions and methods described herein may be used to treat one or more complications arising from low birth weight in mammals and may be administered prior to birth, such as to the mother or to the foetus or after birth, such as to the infant.

Certain embodiments disclosed provide methods of treating complications arising from or related to low birth weight in mammals, such as in humans, pigs, dogs, horses or other livestock, such as in premature infants, in low birth weight infants or in foetuses comprising administering to said mammals:

at least one colony stimulating factor-1 protein (CSF-1), and/or at least one precursor, variant, analogue, derivative thereof or combination thereof, or at least one nucleic acid molecule encoding said at least one colony stimulating factor-1 protein (CSF-1), and/or at least one precursor, variant, analogue, derivative thereof, or combination thereof.

Certain embodiments disclosed include methods of treating complications arising from or related to low birth weight in mammals such as in humans, pigs, horses, dogs or other livestock, such as in premature infants, in low birth weight infants or in foetuses comprising administering to said mammals:

a low birth weight complications-reducing or -limiting amount of at least one colony stimulating factor-1 protein (CSF-1), and/or at least one precursor, variant, analogue, derivative thereof, or combination thereof, or a therapeutically effective amount of at least one nucleic acid molecule encoding a low birth weight complications-reducing or -limiting amount of said at least one colony stimulating factor-1 protein (CSF-1), and/or at least one precursor, variant, analogue, derivative thereof or combination thereof.

Certain embodiments disclosed provide pharmaceutical compositions for treating, reducing or limiting complications arising from or related to low birth weight in mammals, such as in humans, pigs, horses, dogs or other livestock, such as in premature infants, in low birth weight infants or in foetuses comprising administering to said mammals:

a low birth weight complications-reducing or -limiting amount of at least one colony stimulating factor-1 protein (CSF-1), and/or at least one precursor, variant, analogue, derivative thereof or combination thereof, or a therapeutically effective amount of at least one nucleic acid molecule encoding a low birth weight complications-reducing or -limiting amount of said at least one colony stimulating factor-1 protein (CSF-1), and/or at least one precursor, variant, analogue, derivative thereof or combination thereof.

Certain embodiments disclose methods of promoting organ development and/or maturation in mammals, such as in humans, pigs, dogs, horses or other livestock, such as in premature infants, in low birth weight infants or in foetuses are provided. In certain aspects, methods of promoting organ development and/or maturation in mammals are disclosed that comprise the step of administering to the mammal such as the human, pig, horse or other livestock, such as the premature infant, low birth weight infant or foetus:

colony stimulating factor-1 protein (CSF-1), and/or a precursor, variant, analogue, derivative thereof, or combination thereof or a nucleic acid molecule encoding said colony stimulating factor-1 protein (CSF-1), and/or a precursor, variant, analogue, derivative thereof or combination thereof.

In certain aspects, methods of promoting organ development and/or maturation in mammals are disclosed that comprise the step of administering to the mammal such as the human, pig, horse, dogs or other livestock, such as the premature infant, low birth weight infant or foetus:

at least one colony stimulating factor-1 protein (CSF-1), and/or at least one precursor, variant, analogue, derivative thereof or combination thereof, or at least one nucleic acid molecule encoding said colony stimulating factor-1 protein (CSF-1), and/or at least one a precursor, variant, analogue, derivative thereof or combination thereof.

In certain aspects, the methods of promoting organ development in a premature infant, in a low birth weight infant or in a foetus disclosed comprise the step of administering to the premature infant, the low birth weight infants or the foetus:

a premature infant, a low birth weight infant or a foetus organ development-enhancing amount of at least one colony stimulating factor-1 protein (CSF-1), and/or at least one precursor, variant, analogue, derivative thereof or combination thereof, or a therapeutically effective amount of at least one nucleic acid molecule encoding a premature infant, a low birth weight infant or a foetus organ development-enhancing amount of said at least one colony stimulating factor-1 protein (CSF-1), and/or at least one precursor, variant, analogue, derivative thereof or combination thereof.

Certain embodiments disclosed provide pharmaceutical compositions for promoting organ development in a premature infant, in a low birth weight infant or in a foetus that comprise a premature infant, a low birth weight infant or a foetus organ development-enhancing amount of at least one colony stimulating factor-1 protein (CSF-1), and/or at least one precursor, variant, analogue, derivative thereof or combination thereof, or a therapeutically effective amount of at least one nucleic acid molecule encoding a premature infant, a low birth weight infant or a foetus organ development-enhancing amount of said at least one colony stimulating factor-1 protein (CSF-1), and/or at least one precursor, variant, analogue, derivative thereof or combination thereof.

In certain aspects, methods are disclosed that promote growth and/or enhance lung development and/or maturation in mammals, such as in humans, pigs, horses, dogs or other livestock, such as in premature infants, in low birth weight infants or in foetuses. In certain aspects, the methods of promoting lung growth and/or enhancing lung development and/or maturation in mammals, such as in humans, pigs, horses, dogs or other livestock, such as in premature infants, in low birth weight infants or in foetuses comprising administering to said mammals:

colony stimulating factor-1 protein (CSF-1), and/or a precursor, variant, analogue, derivative thereof or combination thereof, or a nucleic acid molecule encoding said colony stimulating factor-1 protein (CSF-1), and/or a precursor, variant, analogue, derivative thereof or combination thereof.

In certain aspects, the methods of promoting lung growth and/or enhancing lung development and/or maturation in a premature infant, in a low birth weight infant or in a foetus disclosed comprise the step of administering to the infant or foetus:

at least one colony stimulating factor-1 protein (CSF-1), and/or at least one precursor, variant, analogue, derivative thereof, or combination thereof, or at least one nucleic acid molecule encoding said at least one colony stimulating factor-1 protein (CSF-1), and/or at least one precursor, variant, analogue, derivative thereof or combination thereof.

In certain aspects, the methods of promoting lung growth and/or enhancing lung development and/or maturation in a premature infant, in a low birth weight infant or in a foetus disclosed comprise the step of administering to the infant or foetus:

a premature infant, a low birth weight infant or a foetus lung growth promoting and/or lung development and/or maturation-enhancing amount of at least one colony stimulating factor-1 protein (CSF-1), and/or at least one precursor, variant, analogue, derivative thereof or combination thereof, or a therapeutically effective amount of at least one nucleic acid molecule encoding a premature infant, a low birth weight infant or a foetus lung growth promoting and/or lung development and/or maturation-enhancing amount of said at least one colony stimulating factor-1 protein (CSF-1), and/or at least one precursor, variant, analogue, derivative thereof or combination thereof.

Certain embodiments disclosed provide pharmaceutical compositions for promoting lung growth and/or enhancing lung development and/or maturation in a premature infant, in a low birth weight infant or in a foetus that comprise a premature infant, a low birth weight infant or a foetus lung growth promoting and/or lung development and/or maturation-enhancing amount of at least one colony stimulating factor-1 protein (CSF-1), and/or at least one precursor, variant, analogue, derivative thereof or combination thereof, or a therapeutically effective amount of at least one nucleic acid molecule encoding a premature infant, a low birth weight infant or a foetus lung growth promoting and/or lung development and/or maturation-enhancing amount of said at least one colony stimulating factor-1 protein (CSF-1), and/or at least one precursor, variant, analogue, derivative thereof or combination thereof.

In certain embodiments, methods of promoting growth, maturation and/or enhancing kidney development in mammals, such as in humans, pigs, horses, dogs or other livestock, such as in premature infants, in low birth weight infants or in foetuses. In certain aspects the methods of promoting growth, maturation and/or enhancing kidney development in mammals, such as in humans, pigs, horses, dogs or other livestock, such as in premature infants, in low birth weight infants or in foetuses comprising administering to said mammals:

colony stimulating factor-1 protein (CSF-1), and/or a precursor, variant, analogue, derivative thereof or combination thereof, or a nucleic acid molecule encoding said colony stimulating factor-1 protein (CSF-1), and/or a precursor, variant, analogue, derivative thereof or combination thereof.

In certain aspects the methods of promoting growth, maturation and/or enhancing kidney development in a premature infant, in a low birth weight infant or in a foetus comprise the step of administering to the infant or foetus;

at least one colony stimulating factor-1 protein (CSF-1), and/or at least one precursor, variant, analogue, derivative thereof, or combination thereof, or at least one nucleic acid molecule encoding said colony stimulating factor-1 protein (CSF-1), and/or at least one precursor, variant, analogue, derivative thereof or combination thereof.

In certain aspects, the methods of growth, maturation and/or enhancing kidney development in a premature infant, in a low birth weight infant or in a foetus disclosed comprise the step of administering to the infant or foetus:

a premature infant, a low birth weight infant or a foetus kidney growth maturation and/or development-enhancing amount of at least one colony stimulating factor-1 protein (CSF-1), and/or a precursor, variant, analogue, derivative thereof or combination thereof, or a therapeutically effective amount of at least one nucleic acid molecule encoding a premature infant, a low birth weight infant or a foetus kidney growth maturation and/or development-enhancing amount of said at least one colony stimulating factor-1 protein (CSF-1), and/or at least one precursor, variant, analogue, derivative thereof or combination thereof.

Certain embodiments disclosed provide pharmaceutical compositions for promoting growth, maturation and/or enhancing kidney development in a premature infant, in a low birth weight infant or in a foetus that comprise a premature infant, a low birth weight infant or a foetus kidney growth maturation and/or development-enhancing amount of at least one colony stimulating factor-1 protein (CSF-1), and/or at least one precursor, variant, analogue, derivative thereof or combination thereof, or a therapeutically effective amount of at least one nucleic acid molecule encoding a premature infant, a low birth weight infant or a foetus kidney growth maturation and/or development-enhancing amount of at least one said colony stimulating factor-1 protein (CSF-1), and/or at least one precursor, variant, analogue, derivative thereof or combination thereof.

In certain aspects, methods are disclosed that promote growth and/or enhance bone development and/or maturation in mammals, such as in humans, pigs, horses, dogs or other livestock, such as in premature infants, in low birth weight infants or in foetuses. In certain aspects, the methods of promoting bone growth and/or enhancing bone development and/or maturation in mammals, such as in humans, pigs, horses, dogs or other livestock, such as in premature infants, in low birth weight infants or in foetuses comprising administering to said mammals:

colony stimulating factor-1 protein (CSF-1), and/or a precursor, variant, analogue, derivative thereof or combination thereof or a nucleic acid molecule encoding said colony stimulating factor-1 protein (CSF-1), and/or a precursor, variant, analogue, derivative thereof or combination.

In certain aspects, the methods of promoting bone growth and/or enhancing bone development and/or maturation in a premature infant, in a low birth weight infant or in a foetus disclosed comprise the step of administering to the infant or foetus:

at least one colony stimulating factor-1 protein (CSF-1), and/or at least one precursor, variant, analogue, derivative thereof or combinations thereof or at least one nucleic acid molecule encoding said at least one colony stimulating factor-1 protein (CSF-1), at least one precursor, at least one variant, at least one analogue, at least one derivative thereof or combinations thereof.

In certain aspects, the methods of promoting bone growth and/or enhancing bone development and/or maturation in a premature infant, in a low birth weight infant or in a foetus disclosed comprise the step of administering to the infant or foetus:

a premature infant, a low birth weight infant or a foetus bone growth promoting and/or bone development and/or maturation-enhancing amount of at least one colony stimulating factor-1 protein (CSF-1), and/or at least one precursor, variant, analogue, derivative thereof or combination thereof or a therapeutically effective amount of at least one nucleic acid molecule encoding a premature infant, a low birth weight infant or a foetus bone growth promoting and/or bone development and/or maturation-enhancing amount of said at least one colony stimulating factor-1 protein (CSF-1), and/or at least one precursor, variant, analogue, derivative thereof or combination thereof.

Certain embodiments disclosed provide pharmaceutical compositions for promoting bone growth and/or enhancing bone development and/or maturation in a premature infant, in a low birth weight infant or in a foetus that comprise a premature infant, a low birth weight infant or a foetus bone growth promoting and/or bone development and/or maturation-enhancing amount of at least one colony stimulating factor-1 protein (CSF-1), and/or a precursor, variant, analogue, derivative thereof or combination thereof, or a therapeutically effective amount of at least one nucleic acid molecule encoding a premature infant, a low birth weight infant or a foetus bone growth promoting and/or bone development and/or maturation-enhancing amount of said at least one colony stimulating factor-1 protein (CSF-1), and/or at least one precursor, variant, analogue, derivative thereof or combination thereof.

DETAILED DESCRIPTION

Figure 1:
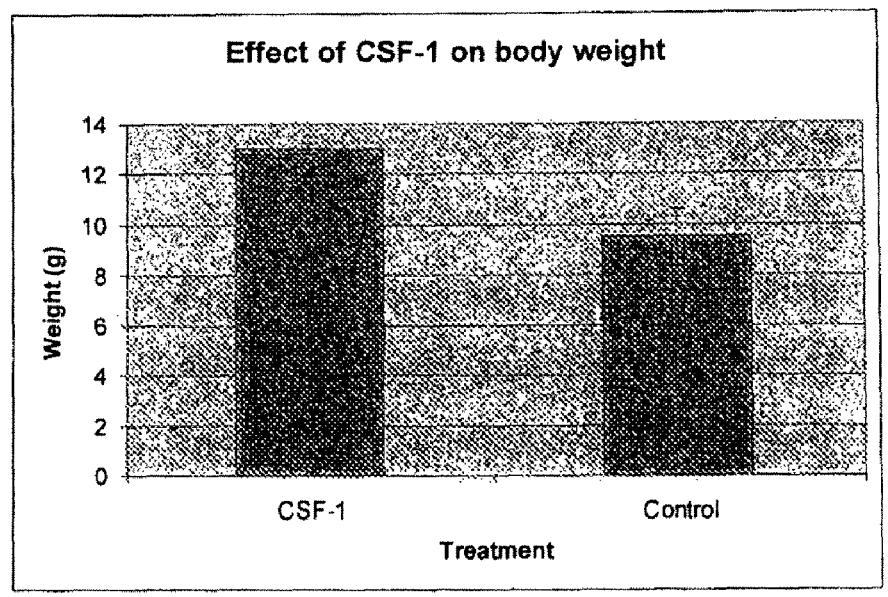
FIG. 1 provides a graph demonstrating the average mouse body weight (n=3/group) in mice receiving CSF-1 compared to litter mate control treated mice.

In general, because of the strong similarities between all placental mammals in terms of organogenesis, the mouse provides an excellent predictive model for organogenesis in humans, pigs, horses, dogs and other placental mammals.

Growth factor known as colony stimulating factor-1 protein (CSF-1) (also known as macrophage colony stimulating factor (M-CSF)) controls the survival, proliferation and differentiation of cells of the monocyte/macrophage lineage, and acts by binding to the CSF-1 receptor (CSF-1R), a cell-surface tyrosine kinase receptor encoded by the c-fms proto-oncogene. Previous studies have shown that c-fms mRNA is found in the placenta, localised to cells of a macrophage specific lineage (Hume, Monkley et al., 1995). The present embodiments relate to and elucidate the role(s) that CSF-1 has in embryonic development. The applicants have found, surprisingly, that in newborn mice, CSF-1 was able to treat complications arising from or related to low birth weight, to promote organ development, and more particularly, increased growth and/or enhanced lung maturation and nephrogenesis in the kidney and increased bone growth and/or enhanced bone maturation in co-occurrence with an overall increase in size and body weight. Lung and kidney development is incomplete in newborn mice, newborn mice, therefore, provide a useful model for lung and kidney development in the human foetus and premature infants. In addition, newborn mice undergo bone and cartilage remodelling and growth postnatally. Thus, as disclosed herein the administration of CSF-1 to premature infants and pregnant mothers at risk of premature birth (or for whom premature birth is desirable) may permit treatment and/or prevention of diseases and conditions associated with underdeveloped organs such as the lungs and kidneys and bone formation.

In certain embodiments, based on studies conducted to elucidate what role(s) CSF-1 might have in embryonic development, the present applicants surprisingly found that in certain embodiments in newborn mice, CSF-1 was able to promote organ development (as reflected in, for some organs, an increase in organ weight), and more particularly, increased growth and/or enhanced nephrogenesis and lung maturation.

In certain embodiments, methods of promoting organ development and/or maturation in a premature infant or foetus, the methods comprising the step of administering to the infant or foetus;

colony stimulating factor-1 protein (CSF-1), or a precursor, variant, analogue or derivative thereof, or a nucleic acid molecule encoding said colony stimulating factor-1 protein (CSF-1), or a precursor, variant, analogue or derivative thereof.

The methods disclosed herein may be used to treat complications arising from or related to low birth weight, to promote the development of one or more organs such as, but not limited to, the lung, kidney, brain, eye and organs of the gastrointestinal (G.I.) tract, in certain aspects in particular the small intestine, and may be used to promote bone growth and development in mammals, such as humans, pigs, horses, dogs and other livestock, such as in premature infants or in foetuses. The organ development that may be achieved by the method disclosed herein can result in cell growth and cell differentiation so as to cause organ maturation (e.g. in terms of organ structure and function) towards that of infants born following a normal, full-term pregnancy and foetal development. The premature infant or foetus treated in accordance with certain embodiments may thereby avoid or defer, for example, developing hypertension and/or reduced renal function following injury later in life, respiratory distress syndrome (RDS) and bronchopulmonary dysplasia, intraventricular hemorrhage and neural development disorders that can lead to learning problems, behavioural problems and cerebral palsy, retinopathy due to abnormal growth of blood vessels, and hearing loss.

In certain embodiments, the methods involve the administration of CSF-1, at least one nucleic acid encoding CSF-1, or combinations thereof. In certain preferred embodiments, the methods disclosed involve the administration of human CSF-1, a least one nucleic acid encoding human CSF-1, or combinations thereof. However, it is also suitable in certain embodiments to administer a precursor, variant, analogue or derivative of CSF-1, at least one nucleic acid encoding same, or combinations thereof. In certain aspects it is preferred to administer, at least one precursor, at least one variant, at least one analogue, at least one derivative of human CSF-1, at least one nucleic acid encoding same, or combinations thereof.

The term "precursor" is to be understood to refer to any molecule that is converted or metabolised within the body to CSF-1. Thus, one example of a suitable CSF-1 precursor is an immature CSF-1 comprising its native, or a heterologous, secretory signal, which can be processed by proteolytic cleavage to produce CSF-1 (i.e. mature CSF-1).

The term "variant" is to be understood to refer to an isoform of CSF-1 encoded by, for example, an allelic variant.

The term "analogue" is to be understood to refer to any molecule that differs from CSF-1 but retains similarity, or substantial similarity, in biological function of CSF-1, in particular the ability to promote organ development. In certain aspects, an analogue may have substantial overall structural similarity with CSF-1 or only structural similarity with one or more regions or domains of CSF-1 responsible for its biological function. Typically, an analogue of CSF-1 will be provided by, or be the result of, the addition of one or more amino acids to the amino acid sequence of CSF-1, deletion of one or more amino acids from the amino acid sequence of CSF-1, and/or substitution of one or more amino acids of the amino acid sequence of CSF-1, and/or combinations thereof. In certain aspects, inversion of amino acids and other mutational changes that result in the alteration of the amino acid sequence are also encompassed. Such an analogue may be prepared by introducing nucleotide changes into a nucleic acid molecule such that the desired amino acid changes are achieved upon expression of the mutagenised nucleic acid molecule, or by otherwise synthesising an amino acid sequence incorporating the desired amino acid changes. The substitution of an amino acid may involve conservative or non-conservative amino acid substitution. By conservative amino acid substitution, it is meant that an amino acid residue is replaced with another amino acid having similar, or substantially similar, characteristics and which does not substantially alter the desired biological function of the protein. Exemplary conservative amino acid substitutions are provided in Table 1 below. In certain aspects, particular conservative substitutions envisaged are: G, A, V, I, L, M; D, E, N, Q; S, C, K, R, H; and P, N-α-alkylamino acids. In certain aspects, conservative amino acid substitutions may be selected on the basis that they do not have any substantial effect on (a) the structure of the peptide backbone in the region of the substitution, (b) the charge or hydrophobicity of the protein at the site of substitution, (c) the bulk of the side chain at the site of substitution, and/or combinations thereof.

TABLE 1

Exemplary conservative amino acid substitutions

| | Conservative Substitutions |
|---|---|
| Ala | Val*, Leu, Ile |
| Arg | Lys*, Gln, Asn |
| Asn | Gln*, His, Lys, Arg, Asp |
| Asp | Glu*, Asn |
| Cys | Ser |
| Gln | Asn*, His, Lys, |
| Glu | Asp*, γ-carboxyglutamic acid (Gla) |
| Gly | Pro |
| His | Asn, Gln, Lys, Arg* |
| Ile | Leu*, Val, Met, Ala, Phe, norleucine (Nle) |
| Leu | Nle, Ile*, Val, Met, Ala, Phe |
| Lys | Arg*, Gln, Asn, ornithine (Orn) |
| Met | Leu*, Ile, Phe, Nle |
| Phe | Leu*, Val, Ile, Ala |
| Pro | Gly*, hydroxyproline (Hyp), Ser, Thr |
| Ser | Thr |
| Thr | Ser |
| Trp | Tyr |
| Tyr | Trp, Phe*, Thr, Ser |
| Val | Ile, Leu*, Met, Phe, Ala, Nle |

*indicates preferred conservative substitutions

In certain aspects, where an analogue is prepared by synthesis, the analogue may also include an amino acid or amino acids not encoded by the genetic code, such as γ-carboxyglutamic acid and hydroxyproline. For example, D-amino acids rather than L-amino acids may be included. A list of amino acids not encoded by the genetic code is provided in Table 2. In a certain preferred embodiments, the analogue is a mimetic of CSF-1 such as a peptido-mimetic. However, it is not always necessary that an analogue of CSF-1 have amino acid sequence identity and/or similarity. In certain aspects an analogue may not be proteinaceous at all. In certain embodiments an analogue may have at least 75%, such as at least 80%, at least 85%, at least 90%, at least 91%, at least 92%, at least 93%, at least 94%, at least 95%, at least 96%, at least 97%, at least 98% or at least 99% homology with CSF-1.

TABLE 2

List of amino acids not encoded by the genetic code

| | | |
|---|---|---|
| α-aminobutyric acid | D-α-methylhistidine | L-N-methyl-t-butylglycine |
| α-amino-α-methylbutyrate | D-α-methylisoleucine | L-norleucine |
| Aminocyclopropane-carboxylate | D-α-methylleucine | L-norvaline |
| Aminoisobutyric acid | D-α-methyllysine | α-methyl-aminoisobutyrate |
| Aminonorbornyl-carboxylate | D-α-methylmethionine | α-methyl-α-aminobutyrate |
| Cyclohexylalanine | D-α-methylornithine | α-methylcyclohexyl alanine |
| Cyclopentylalanine | D-α-methylphenylalanine | α-methylcylcopentyl alanine |
| L-N-methylisoleucine | D-α-methylproline | α-methyl-α-napthyl alanine |
| D-alanine | D-α-methylserine | α-methylpenicillamine |
| D-arginine | D-α-methylthreonine | N-(4-aminobutyl)glycine |
| D-aspartic acid | D-α-methyltryptophan | N-(2-aminoethyl)glycine |
| D-cysteine | L-N-methylalanine | N-(3-aminopropyl)glycine |
| D-glutamate | L-N-methylarginine | N-amino-α-methyl butyrate |
| D-glutamic acid | L-N-methylasparagine | α-napthylalanine |
| D-histidine | L-N-methylaspartic acid | N-benzylglycine |
| D-isoleucine | L-N-methylcysteine | N-(2-carbamylediyl) glycine |
| D-leucine | L-N-methylglutamine | N-(carbamylmethyl) glycine |
| D-lysine | L-N-methylglutamic acid | N-(2-carboxyethyl)glycine |
| D-methionine | L-N-methylhistidine | N-(carboxymethyl)glycine |
| D-ornithine | L-N-methylleucine | N-cyclobutylglycine |
| D-phenylalanine | L-N-methyllysine | N-(N-(3,3-diphenylpropyl carbamylmethyl)glycine |
| D-proline | L-N-methylmethionine | N-(N-(2,2-diphenylethyl carbamylmethyl)glycine |
| D-serine | L-N-methylnorleucine | 1-carboxy-1-(2,2-diphenyl-ethylamino)cyclopropane |
| D-threonine | L-N-methylnorvaline | L-α-methyltryptophan |
| D-tryptophan | L-N-methylornithine | N-cycloheptylglycine |
| D-tyrosine | L-N-methylphenylalanine | N-cyclohexylglycine |
| D-valine | L-N-methylproline | N-cyclodecylglycine |
| D-α-methylalanine | L-N-medlyserine | L-α-methylnorleucine |
| D-α-methylarginine | L-N-methylserine | L-α-methylornithine |
| D-α-methylasparagine | L-N-methyltryptophan | L-α-methylproline |
| D-α-methylaspartate | L-N-methyltyrosine | L-α-methylthreonine |
| D-α-methylcysteine | L-N-methylvaline | L-α-methyltyrosine |
| D-α-methylglutamine | L-N-methylethyl-glycine | L-N-methylhomo-phenylalanine |

TABLE 2-continued

List of amino acids not encoded by the genetic code

| D-α-methyltyrosine | L-α-methylleucine | L-α-methylserine |
| L-α-methylmethionine | L-α-methyllysine | L-α-methylphenylalanine |
| L-α-methylnorvatine | L-α-methylvaline | |

The term "derivative" is to be understood to refer to any molecule that is derived (substantially derived) or obtained (substantially obtained) from CSF-1, but retains similarity, or substantial similarity, in biological function of CSF-1. In certain aspects, the biological function is the ability to promote organ development. A derivative may, for instance, be provided as a result of cleavage of CSF-1 to produce biologically-active fragments, cyclisation, bioconjugation and/or coupling with one or more additional moieties that improve, for example, solubility, stability or biological half-life, or which act as a label for subsequent detection or the like. A derivative may also result from post-translational or post-synthesis modification such as the attachment of carbohydrate moieties, or chemical reaction(s) resulting in structural modification(s) such as alkylation or acetylation of an amino acid(s) or other changes involving the formation of chemical bonds. In a particularly preferred embodiment of a derivative suitable for use in the present invention, the derivative is the mature domain of CSF-1. In another preferred embodiment of a derivative suitable for use in the methods disclosed herein, the derivative is a biologically active, C-terminal fragment of CSF-1 (e.g. a CSF-1 fragment comprising the C-terminal amino acids 1 to 150 of the 536 amino acid protein). Further embodiments of a derivative of CSF-1 include CSF-1 comprising chemically modified side chains (e.g. pegylation of lysyl ε-amino groups), C- and/or N-termini (e.g. acylation of the N-terminal with acetic anhydride), or linked to various carriers (e.g. human serum albumin or histidine ($His_6$) tag).

CSF-1 produced from synthetic protein synthesis and chemical ligation may be used as a source for delivery of large amounts of protein to animals or infants. These synthesized protein analogues may have improved potency or pharmacokinetic properties in comparison to natural CSF-1. CSF-1 protein may be made by first making individual peptide segments of the protein using solid-phase peptide synthesis (SPPS) and then after purification, joining the segments chemically, or via ligation, in solution to form the full-length polypeptide. To facilitate the ligation of individual peptide segments an N-terminal cysteine residue (generally occurring naturally in the protein sequence) and a C-terminal thioester (prepared on-resin) may be needed. After synthesis, the unfolded full-length CSF-1 polypeptide may be folded into its biologically active conformation.

Preferably, certain embodiments disclosed involve the administration of at least one recombinant human CSF-1 (rhCSF-1), in particular, bacterially-expressed, non-glycosylated recombinant human CSF-1.

CSF-1, or a precursor, variant, analogue or derivative thereof, may be administered to the premature infant or foetus by any effective method, some of which are known. For example, for the premature infant, the route of administration can be selected from, for example, intramuscular (i.m.), intravenous (i.v.), topical, such as inhalational administration, intratracheal, subcutaneous (s.c.) administration and/or combinations thereof. On the other hand, for the foetus, the route of administration may be selected from i.m., i.v., s.c., intrauterine (i.u.), oral, inhalational administration to the pregnant mother, and/or combinations thereof.

In some embodiments, rather then systemic administration, it may be desirable for the route of administration to be localized to one or more specific organs or portions of the body, such as by direct application of the therapeutic to the target treatment area or areas. In some embodiments, the composition may be an immediate release dosage form. In other embodiments the composition may be a time release dosage form, including an implantable controlled release form. In some embodiments, the dosage forms may include tablets, dispersions, suspensions, solutions, injections, syrups, troches, capsules suppositories, aerosols, transdermal patches and the like.

Certain embodiments may be administered to ventilated premature infants using aerosol delivery. "Preterm" or "premature" birth can be defined as delivery before approximately the thirty-seventh week of pregnancy. Preteen deliveries can be further delineated as either "very preterm" (before approximately the thirty-third week) or "moderately preterm" (between the approximately thirty-third and approximately the thirty-sixth weeks). Mechanical ventilation that is heated or non-heated; and humidified or non-humidified may be performed in infants. Because of the small tidal volumes and high respiratory rates required for an infant, ventilation may be time or pressure cycled, with a continuous flow of gas circulating through the ventilator circuit.

Certain embodiments of the composition and methods disclosed may be include delivery of CSF-1 with ventilation by aerosol delivery using either a vibrating mesh nebulizer, a jet nebuliser, a metered dose inhaler (MDI), an ultrasonic nebulizer, or an electric pump nebuliser. For example, CSF-1 may be administered in the nebulizer as a bolus dose before the initiation of positive pressure ventilation. In another example CSF-1 may be delivered using continuous feed through an infusion set into a nebulizer. Such a method will allow dosing of aerosol at different rates by adjusting the flow of the drug/unit of time into the nebulizer. Nebulization of certain embodiments disclosed herein may ensure more effective drug delivery to, for example, the lung alveoli of the premature infants.

In certain embodiments, nebulization treatment may be delivered as soon as possible after birth and delivered either intermittently or with continuous aerosol therapy. Continuous nebulization therapy may involve the delivery of prescribed dose of, for example, CSF-1 in diluents or sterile saline or phosphate buffered-saline over 8 hour periods. CSF-1 may be delivered with a small volume-limited or large-volume nebuliser with infusion pump. The volume of CSF-1 to be delivered to infants in the nebulizer may be in the range of 5-15 ml. The CSF-1 may be added to the pediatric nebulizer unit in the inspiratory limb of the ventilator circuit about 10-30 cm away from the patient wye.

The nebulisers may be placed in the ventilator manifold and set to deliver a CSF-1 to an infant at a dose ranging from 0.01-1000 μg/hour of CSF-1 continuously over 8 hours for 1 day, 2 days, 3 days, 4 days, 5 days, 6 days or 7 consecutive days. Typically, such an amount may be, in the case of administration to the premature infant, in the range of about 0.1 to 500 μg/h, about 0.05 to 500 μg/h, about 0.2 to 400 μg/h, 0.1 to 1000 μg/h, about 0.05 to 1000 μg/h, about 0.1 to 1000 μg/h, about 0.5 to 300 μg/h, about 0.75 to 200 μg/h about 1 to 100 μg/h, about 1 to 100 μg/h about 1.25 to 30 μg/h, or about 0.5 to 50 μg/h and, in certain aspects about 0.5 to 200 μg/h, about 0.05 to 100 μg/h, about 0.25 to 150 μg/h, about 0.5 to 50 μg/h, about 1 to 100 μg/h, about 0.75 to 200 μg/h, about 0.5 to 30 μg/h, or about 0.1 to 75 μg/h.

Additionally, in some embodiments, the nebulisers may deliver CSF-1 to infants at a dose ranging from 0.01-1000 mg/hour of CSF-1. CSF-1 to the infants at a dose ranging from 0.01-1000 mg/hour of CSF-1 continuously over 8 hours for 1 day, 2 days, 3 days, 4 days, 5 days, 6 days or 7 consecutive days. Typically, such an amount may be, in the case of administration to the premature infant, in the range of about 0.1 to 500 mg/h, about 0.05 to 500 mg/h, about 0.2 to 400 mg/h, 0.1 to 1000 mg/h, about 0.05 to 1000 mg/h, about 0.1 to 1000 mg/h, about 0.2 to 400 mg/h, about 0.5 to 300 mg/h, about 0.75 to 200 mg/h about 1 to 100 mg/h, about 1 to 100 mg/h about 1.25 to 30 mg/h, or about 0.5 to 50 mg/h and, in certain aspects about 0.5 to 200 mg/h, about 0.05 to 100 mg/h, about 0.25 to 150 mg/h, about 0.5 to 50 mg/h, about 1 to 100 mg/h, about 0.75 to 200 mg/h, about 0.5 to 30 mg/h, or about 0.1 to 75 mg/h.

Alternatively, in some embodiments, CSF-1 and/or a precursor, variant, analogue, derivative thereof or combination thereof, may be administered to a premature infant directly into the bloodstream by intramuscular (i.m.), intravenous (i.v.), subcutaneous (s.c.) administration and/or combinations thereof. The most familiar type of vascular access is a peripheral intravenous line (PIV) attached to an i.v. pump. In newborns, PIVs often may be placed in veins of the hand, foot, or scalp that may enable delivery of CSF-1 in combination with fluids, nutrients or other pharmaceutical agents. The PIV may enable the continuous infusion or pulse infusion of CSF-1 for hours to days. CSF-1 may be delivered by i.v infusion to the infants at a dose ranging from 0.01-1000 µg/hour of CSF-1 continuously over 8 hours for 1 day, 2 days, 3 days, 4 days, 5 days, 6 days or 7 consecutive days. Typically, such an amount may be, in the case of administration to the premature infant, in the range of about 0.1 to 500 µg/h, about 0.05 to 500 µg/h, about 0.2 to 400 µg/h, 0.1 to 1000 µg/h, about 0.05 to 1000 µg/h, about 0.1 to 1000 µg/h, about 0.5 to 300 µg/h, about 0.75 to 200 µg/h about 1 to 100 µg/h, about 1 to 100 µg/h about 1.25 to 30 µg/h, or about 0.5 to 50 µg/h and, in certain aspects about 0.5 to 200 µg/h, about 0.05 to 100 µg/h, about 0.25 to 150 µg/h, about 0.5 to 50 µg/h, about 1 to 100 µg/h, about 0.75 to 200 µg/h, about 0.5 to 30 µg/h, or about 0.1 to 75 µg/h.

CSF-1 may be delivered to infants by i.v infusion at a dose ranging from 0.01-1000 mg/hour of CSF-1 at a dose ranging from 0.01-1000 mg/hour of CSF-1 continuously over 8 hours for 1 day, 2 days, 3 days, 4 days, 5 days, 6 days or 7 consecutive days. CSF-1 may be delivered in the range of about 0.1 to 500 mg/h, about 0.05 to 500 mg/h, about 0.2 to 400 mg/h, 0.1 to 1000 mg/h, about 0.05 to 1000 mg/h, about 0.1 to 1000 mg/h, about 0.2 to 400 mg/h, about 0.5 to 300 mg/h, about 0.75 to 200 mg/h about 1 to 100 mg/h, about 1 to 100 mg/h about 1.25 to 30 mg/h, or about 0.5 to 50 mg/h and, in certain aspects about 0.5 to 200 mg/h, about 0.05 to 100 mg/h, about 0.25 to 150 mg/h, about 0.5 to 50 mg/h, about 1 to 100 mg/h, about 0.75 to 200 mg/h, about 0.5 to 30 mg/h, or about 0.1 to 75 mg/h.

In some embodiments, the CSF-1, at least one precursor, at least one variant, at least one analogue, at least one derivative, or combinations thereof, may be administered in the form of a composition comprising a carrier (e.g. a pharmaceutically acceptable vehicle or diluent such as saline). Infants that are intubated may receive CSF-1 as an aerosol with nebulizer treatment before or in combination with another pharmaceutical agent including but not limited to surfactants such as artificial or natural surfactants, such as EXOSURF, PUMACTANT, KL-4, VENTICUTE. ALVEOFACT, CUROSURF, INFASURF or SURVANTA, anti-inflammatory agents or corticosteroids, fluids for hydration, heparin, albuterol, antibiotics, ibuprofen, nutritional supplements, vitamin supplements, mineral supplements, sildenafil, other colony stimulating factors such as G-CSF or GM-CSF, and/or IGF-I, IGF-II, HGF, EGF, or mixtures thereof.

In some embodiments, CSF-1 may be delivered to the foetus via the pregnant woman by i.v bolus injection typically at a concentration range of 0.1-1 g/kg body weight. The exact amount may vary depending upon a variety of factors including the relative activity, metabolic stability and length of action of the CSF-1, precursor, variant, analogue or derivative thereof, the route and time of administration, the degree, or likely degree, of organ underdevelopment, and, in the case of the foetus, the general health of the pregnant mother.

Alternatively, in some embodiments, CSF-1 may be delivered by aerosol nebulisation with or without ventilation. CSF-1 may be administered in the nebulizer as a bolus dose before the initiation of positive pressure ventilation. Alternatively, CSF-1 may be delivered by continuous feed through an infusion set into a nebulizer. The doses and timing for CSF-1 delivery may be similar to infants described above.

In some embodiments, in pregnant warm blooded animals, such as mares, pigs, cattles, dogs and other livestock, CSF-1 may be delivered to the foetus by bolus injection into the bloodstream of the mother using intramuscular, intravenous, or subcutaneous administration or combinations of the above at a concentration range typically from 0.1-1 g/kg of body weight. Alternatively, in other embodiments, CSF-1 may be delivered to such animals or to infant animals by aerosol nebulisation with or without ventilation by administration of a bolus in the nebuliser before initiation of positive pressure or by using a continuous feed through an infusion set into a nebuliser. The doses and timing for CSF-1 delivery may be similar to human infants described above.

In some embodiments, the CSF-1, at least one precursor, at least one variant, at least one analogue, at least one derivative, or combinations thereof, may be administered in the form of a composition comprising a carrier (e.g. a pharmaceutically acceptable excipient, vehicle or diluent). Such compositions may further comprise other therapeutic agents (e.g. IGF-I, IGF-II, HGF, EGF, or mixtures thereof) and may be formulated by, for example, employing conventional solid or liquid excipients, vehicles, diluents or combinations thereof, as well as pharmaceutical additives of a type appropriate to the mode of desired administration (for example, excipients, binders, preservatives, stabilisers, flavours, colorants, buffers etc.). Non-limiting examples of suitable excipients, vehicles and diluents may be found in Gennaro, Alfonso, *Remington's Pharmaceutical Sciences,* 18$^{th}$ edition, Mack Publishing Co. (1990), in Gennaro, Alfonso, *Remington: The Science and Practice of Pharmacy,* 19$^{th}$ edition (1995) and, 20$^{th}$ edition (2003) and/or in University of the Sciences in Philadelphia (editor) *Remington: The Science and Practice of Pharmacy* and 21$^{st}$ edition (2005), the entire contents of each of which is hereby incorporated by reference. Examples of some excipients include sterile liquids, such as water and oils, including those of petroleum, animal, vegetable or synthetic origin, such as peanut oil, soybean oil, mineral oil, sesame oil, saline solutions, aqueous dextrose solutions, aqueous glycerol solutions, buffers, proteins such as serum albumin, amino acids such as aspartic acid, glutamic acid, lysine, arginine, glycine, histidine, peptides, carbohydrates such as saccharides, polymeric additives, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents, or combinations thereof. Examples of some buffers that may be used include salts prepared from an inorganic acid such as mineral acid salts, such as hydrochlorides, bromides, and sulfates and salts prepared from an organic acid or base, such as salts of citric acid, propionic acid, malonic acid, ascorbic acid, gluconic acid, carbonic acid, tartaric acid, succinic acid, acetic acid, or phthalic acid or Tris, tromethamine hydrochloride, phosphate buffers, or combinations thereof.

The CSF-1, at least one precursor, at least one variant, at least one analogue, at least one derivative, or combinations thereof, may be administered in any amount that is effective in treating complications arising from low birth weight in mammals, such as humans, pigs, horses, dogs or other livestock, such as in premature infants or foetuses, in promoting organ development in the premature infant or foetus and/or in promoting bone growth and/or enhancing bone development and/or maturation in mammals, such as humans, pigs, horses, dogs or other livestock, such as in premature infants or foetuses. Typically, such an amount will be, in the case of administration to the premature infant, in the range of about 0.1 to 500 µg/kg/day, about 0.05 to 500 µg/kg/day, about 0.1 to 500 µg/kg/day, about 0.2 to 400 µg/kg/day, about 0.5 to 300 µg/kg/day, about 0.75 to 200 µg/kg/day about 1 to 100 µg/kg/day, about 1 to 100 µg/kg/day about 1.25 to 30 µg/kg/day, or about 0.5 to 50 µg/kg/day and, in certain aspects more preferably, about 0.5 to 200 µg/day, about 0.05 to 100 µg/kg/day, about 0.25 to 150 µg/kg/day, about 0.5 to 50 µg/kg/day, about 1 to 100 µg/kg/day, about 0.75 to 200 µg/kg/day, about 0.5 to 30 µg/kg/day, or about 0.1 to 75 µg/kg/day and for the foetus (where administration is via the pregnant mother). However, the exact amount may substantially vary depending upon a variety of factors including, but not limited to, the relative activity, metabolic stability and length of action of the CSF-1, at least one precursor, at least one variant, at least one analogue, at least one derivative, or combinations thereof, the route and time of administration, the degree, or likely degree, of organ underdevelopment, the type and severity of complications arising from the low birth weight, the age of the foetus or premature infant and, in the case of the foetus, the general health of the pregnant mother.

Administration of the CSF-1, at least one precursor, at least one variant, at least one analogue, at least one derivative, or combinations thereof, to the premature infant may commence upon birth and continue until a desired level of organ development is observed. Thus, for the lung, a desired level of lung development may be achieved when the saccular phase has been completed and/or the infant no longer requires a mechanical ventilator. For the kidney, a desired level or organ development may be achieved when renal function has been improved and/or the numbers of nephrons has been increased since birth. For the foetus, administration of the CSF-1, at least one precursor, at least one variant, at least one analogue, at least one derivative thereof, or combinations thereof, may commence from about gestational week 4, about gestational week 5, about gestational week 7, about gestational week 10, about gestational week 12, about gestational week 14, or about gestational week 19, but in certain aspects preferably, commences after about week 20, about week 22, about week 24, or about week 26.

Certain embodiments disclosed also encompasses the administration of at least one nucleic acid molecule encoding CSF-1, at least one precursor, at least one variant, at least one analogue, at least one derivative thereof, or combinations thereof, such that the CSF-1, at least one precursor, at least one variant, at least one analogue, at least one derivative thereof, or combinations thereof, are expressed from the nucleic acid molecule by the premature infant or foetus (and/or pregnant mother).

In certain embodiments, suitable nucleic acid molecules may be single or double stranded, such as mRNA, ssRNA, dsRNA, ssDNA and dsDNA. However, in certain preferred aspects, the nucleic acid molecule will be dsDNA.

The nucleic acid molecule may be incorporated into an expression construct or vector in accordance with any effective method, some of which are known. Typically, in certain aspects the nucleic acid molecule will be introduced into such an expression construct or vector such that transcription of the nucleic acid molecule is driven by a promoter sequence provided by the expression construct or vector. In certain aspects it is preferred that the expression construct or vector is adapted for expression in mammalian cells, tissues or organs such as lung and/or kidney cells.

In certain aspects it is preferred that the nucleic acid molecule is incorporated into at least one viral vector such as an adenovirus, lentivirus or poxvirus vector.

The nucleic acid molecule may be administered to the premature infant or foetus (via the pregnant mother) by any effective method, some of which are well know (e.g. liposome-mediated transfection, or for viral vectors, viral transformation).

Administration of the at least one nucleic acid molecule encoding the CSF-1, at least one precursor, at least one variant, at least one analogue, at least one derivative thereof, or combinations thereof, to the premature infant may occur upon birth, whereas for the foetus, administration of the at least one nucleic acid molecule encoding the CSF-1, at least one precursor, at least one variant, at least one analogue, at least one derivative thereof, or combinations thereof, may occur from about gestational week 4, about gestational week 5, about gestational week 7, about gestational week 10, about gestational week 12, about gestational week 14, or about gestational week 19, but in certain aspects preferably, commences after about week 20, about week 22, about week 24, or about week 26.

Certain methods disclosed are particularly suitable for increasing growth and/or enhancing lung maturation and nephrogenesis in the kidney.

In certain aspects disclosed, the methods of promoting growth and/or enhanced lung development and/or maturation in a premature infant or foetus, comprise the step of administering to the infant or foetus;
  at least one colony stimulating factor-1 protein (CSF-1), or at least one precursor, at least one variant, at least one analogue, at least one derivative thereof, or combinations thereof, or
  at least one nucleic acid molecule encoding said colony stimulating factor-1 protein (CSF-1), at least one precursor, at least one variant, at least one analogue, at least one derivative thereof, or combinations thereof.

In certain aspects disclosed, the methods of promoting growth and/or enhanced lung development and/or maturation in a premature infant or foetus, comprise the step of administering to the infant or foetus;
  colony stimulating factor-1 protein (CSF-1), or precursor, variant, analogue, or derivative thereof or
  nucleic acid molecule encoding said colony stimulating factor-1 protein (CSF-1), precursor, variant, analogue, or derivative thereof.

And, in certain aspects disclosed a method of promoting growth, maturation and/or enhanced kidney development in a premature infant or foetus is provided, said method comprising the step of administering to the infant or foetus;
  colony stimulating factor-1 protein (CSF-1), or a precursor, variant, analogue or derivative thereof, or
  a nucleic acid molecule encoding said colony stimulating factor-1 protein (CSF-1), or a precursor, variant, analogue or derivative thereof.

In certain aspects disclosed, methods are provided for promoting growth, maturation and/or enhanced kidney development in a premature infant or foetus, comprising the step of administering to the infant or foetus;

at least one colony stimulating factor-1 protein (CSF-1), at least one precursor, at least one variant, at least one analogue, at least one derivative thereof or combinations thereof, or at least one nucleic acid molecule encoding said colony stimulating factor-1 protein (CSF-1), at least one precursor, at least one variant, at least one analogue, at least one derivative thereof, or combinations thereof.

It is anticipated that the certain methods disclosed may be equally applicable to newborn non-human animals and non-human foetuses. In particular, it is anticipated that the methods of the invention might be used in relation to warm blooded animal, for example. But not limited to, thoroughbred horses, stud animals and companion animals such as dogs and cats.

In order that the nature of the present inventions may be more clearly understood, preferred forms thereof will now be described with reference to the following non-limiting examples.

In some embodiments, the methods of treating complications arising from low birth weight in mammals, such as humans, pigs, horses, dogs or other livestock, such as in premature infants or foetuses, in promoting organ development in the premature infant or foetus and/or in promoting bone growth and/or enhancing bone development and/or maturation in mammals, such as humans, pigs, horses, dogs or other livestock, such as in premature infants or foetuses may include co-treatment with other therapeutic modalities.

For example, in some embodiments, prior to birth the methods may include treatment of the mother by administering to the mother at least one colony stimulating factor-1 protein (CSF-1), at least one precursor, at least one variant, at least one analogue, at least one derivative thereof or combinations thereof, or at least one nucleic acid molecule encoding said colony stimulating factor-1 protein (CSF-1), at least one precursor, at least one variant, at least one analogue, at least one derivative thereof, or combinations thereof;

in combination with treatment with one or more drugs or other substances to treat an underlying cause of low birth weight or complications resulting from low birth weight, such as drugs for hypertension, infections or diabetes, corticosteroids, tocolytics, nutritional supplements, vitamin supplements, mineral supplements, albuterol, antibiotics, heparin, other colony stimulating factors such as G-CSF or GM-CSF, surfactants such as artificial or natural surfactants, such as EXOSURF, PUMACTANT, KL-4, VENTICUTE. ALVEOFACT, CUROSURF, INFASURF or SURVANTA, IGF-I, IGF-II, HGF, EGF, sildenafil, ibuprofen or in combination with surgical treatment of the mother and/or fetus.

In some embodiments, prior to birth the treatment of the mother may include treatment in a dosage form that enhances transplacental drug delivery, such as using a liposomal form of the administered treatment. Such liposomal forms may be created having a variety of sizes, charges and lipid compositions. In some embodiments, such liposomal forms may be anionic small unilamellar liposomes.

In some embodiments after birth, the methods herein may include administering to the premature or low birth weight infant at least one colony stimulating factor-1 protein (CSF-1), at least one precursor, at least one variant, at least one analogue, at least one derivative thereof or combinations thereof, or at least one nucleic acid molecule encoding said colony stimulating factor-1 protein (CSF-1), at least one precursor, at least one variant, at least one analogue, at least one derivative thereof, or combinations thereof;

in combination with treatment with one or more drugs or other substances to treat an underlying cause or complication of low birth weight, such as co-administration of surfactant therapy, such as administration of surfactant, such as artificial or natural surfactants, such as EXOSURF, PUMACTANT, KL-4, VENTICUTE. ALVEOFACT, CUROSURF, INFASURF or SURVANTA, albuterol, heparin, sildenafil, ibuprofen, nutritional supplementation, vitamin and/or mineral supplementation, surgery, IGF-I, IGF-II, HGF, EGF, antibiotic therapy, other colony stimulating factors such as G-CSF or GM-CSF, other drug therapy to treat any complications of low birth weight.

In some embodiments, the CSF-1 may be provided as a kit, such as at least one colony stimulating factor-1 protein (CSF-1), at least one precursor, at least one variant, at least one analogue, at least one derivative thereof or combinations thereof, or at least one nucleic acid molecule encoding said colony stimulating factor-1 protein (CSF-1), at least one precursor, at least one variant, at least one analogue, at least one derivative thereof, or combinations thereof in conjunction with instructions for administration, including dosing instructions, adverse event information and adverse interaction information, other dosing equipment or coadministration therapy-related drugs, equipment and/or instructions.

For example, in some embodiments of the kits, at least one colony stimulating factor-1 protein (CSF-1), at least one precursor, at least one variant, at least one analogue, at least one derivative thereof or combinations thereof, may be provided as an ampule that may be added to a nebulisation unit or as a pre-dosed nebulisation system that attaches to a ventilator system for premature babies. In some embodiments of the kits, at least one colony stimulating factor-1 protein (CSF-1), at least one precursor, at least one variant, at least one analogue, at least one derivative thereof or combinations thereof, may be provided in pre-dosed syringes, with infant-specific i.v. lines and infant-sized needles or other administration devices. In some embodiments, CSF-1 kits may be provided as a mixture of at least one colony stimulating factor-1 protein (CSF-1), at least one precursor, at least one variant, at least one analogue, at least one derivative thereof or combinations thereof with saline, buffered saline or other diluent and/or as a mixture with other colony stimulating factors, such as G-CSF and/or CM-CSF, drugs such as albuterol, antibiotics, or IGF-I, IGF-II, HGF, EGF, or a surfactant or mixtures thereof.

EXAMPLES

Example 1

Materials and Methods

Newborn Mouse Analysis

C57/B16 mice were time-mated and the mouse pups given three intraperitoneal (i.p.) injections of recombinant human CSF-1 (Chiron Corporation, Emeryville, Calif., USA) at days 1, 2 and 3 after birth. The CSF-1 was administered at a dose of 1 μg/g body weight at a concentration of 1 μg/ml where the final volume did not exceed 50 μl per injection. Litter mate aged-matched control mice received vehicle (phosphate buffered saline) control injections of the same volume. The CSF-1-treated mouse pups were toe and tail clipped for identification and returned to their mothers. The CSF-1-treated mouse pups and the control-treated pups were killed at day 29 for light microscopy of kidney and lung histology and estimation of glomerular number.

Histology

Kidney and lung tissue was taken from CSF-1-treated and litter mate control-treated mice, immersion fixed in 4% paraformaldehyde and processed on short cycle before embedding into paraffin for histological analysis.

The paraffin-embedded kidneys were each sectioned at 4 microns using a microtome (Leitz Wetzlar, Germany), and the sections were then placed on poly-L-lysine slides and left to adhere for 3 hours at 70° C. The slides were dewaxed in xylene, rehydrated through graded alcohols to water before staining with haematoxylin and eosin by standard methods.

Stereological Assessment of Glomerular Number and Kidney Volume

At day 29, mice with/without delivery of CSF-1 were killed and their kidneys removed and processed for methacrylate embedding and subsequent stereological counting. The processing involved placing the kidneys into 10% formalin for 48 hours, 70% ethanol overnight, and then three one hour washes with 100% ethanol followed by butanol overnight and 72 hours in infiltration solution (Technovik 7100, Electron Microscopy Sciences, QLD). Kidneys were then embedded in methacrylate resin (Technovik 7100) and left to set for three days. Once set, the backs of blocks were made using Technovik 3040 solution (Technovik, Electron Microscopy Sciences, QLD) and allowed to set for one hour. Sections were then serial sectioned at 20 µm using a microtome, and every 10th and 11th section was collected beginning at a random number.

Sections were stained using periodic acid-Schiff (PAS) staining, however the time in reagents was extended compared to a standard paraffin protocol, due to the slow rate of penetration through the resin.

Stereological counting was performed firstly on a microfische reader to determine kidney volume using the Cavalieri Principal (Kett, M M et al., 1996). Complete sections were used for nephron number estimation using a physical dissector/fractionator combination (Bertram, J F, 1995)—whereby pairs of sections are projected onto an unbiased 2×2 cm counting grid. Grid points that lay upon kidney tissue, glomeruli and renal corpuscles were tabulated, as were glomeruli disappearing events across each slide. Using a formula, the nephron number was estimated.

Results and Discussion

Figure 2:
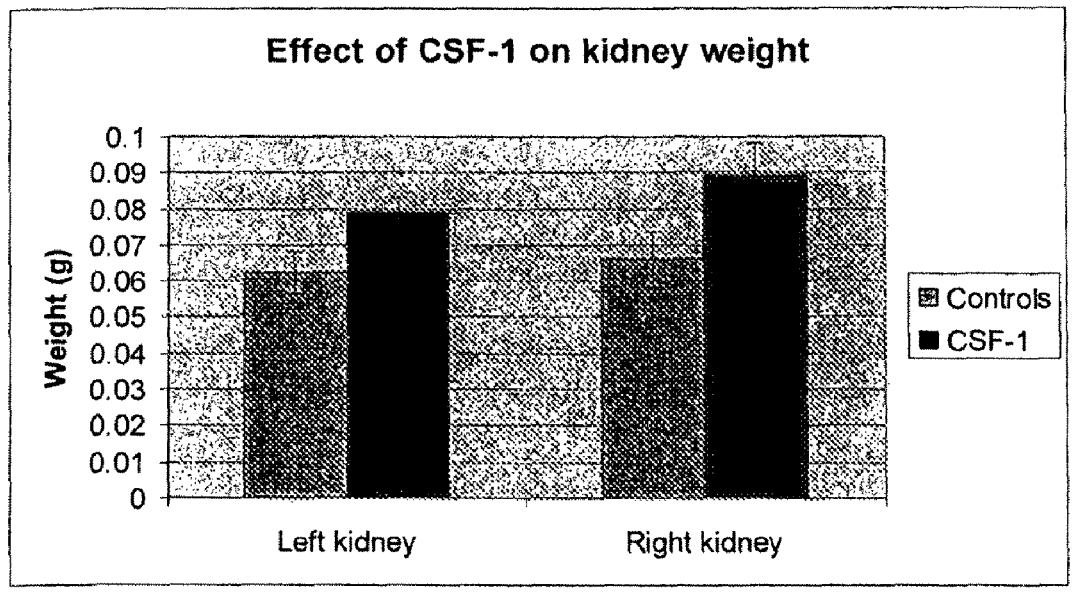
FIG. 2 provides a graph showing the effect on kidney weight of CSF-1 delivery to newborn mouse pups.
Figure 3:
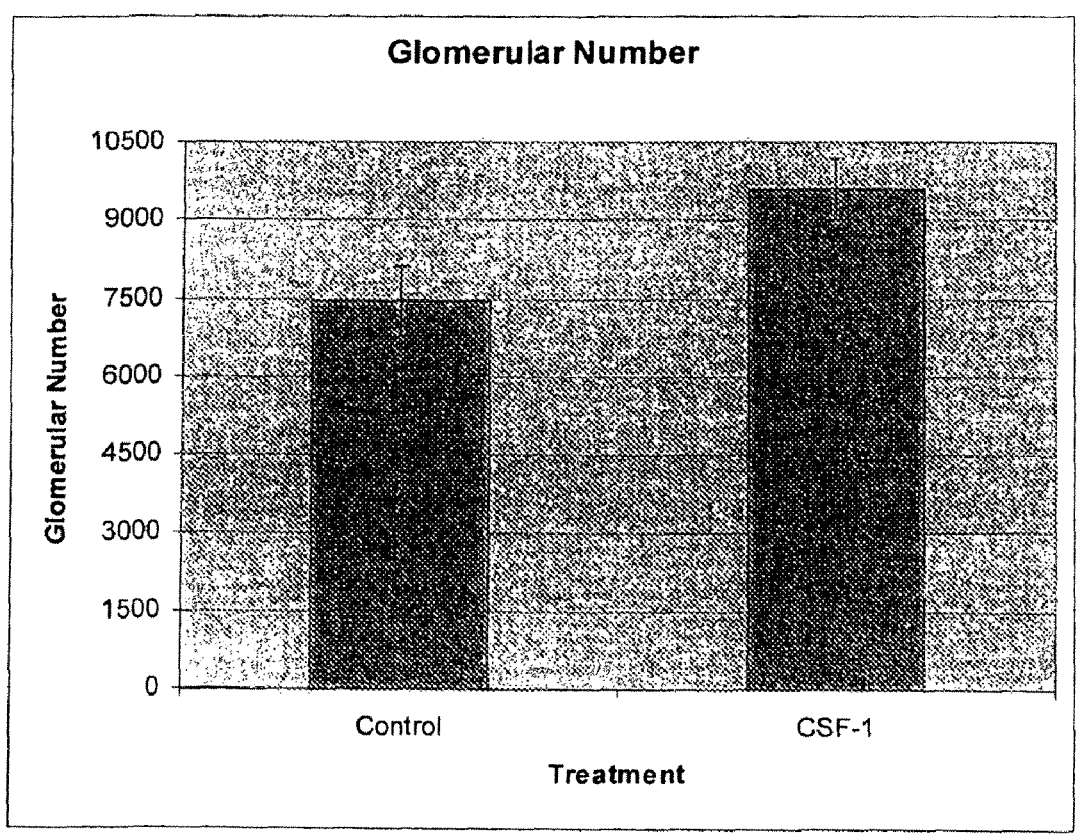
FIG. 3 provides a graph showing a stereological estimation of glomerular number in the kidneys from mice receiving CSF-1 or phosphate buffered saline (PBS).

The administration of CSF-1 (1 µg/g body weight) was given to mouse pups at Day 1, 2 and 3 after birth. In CSF-1-treated mice, there was an overall increase in body weight (FIG. 1) and individual kidney weights (FIG. 2). Mice killed at day 29 we observed to have a 37% increase in overall body weight compared to age-matched litter mates. CSF-1-treated mice had a 27% and 33% increase in left and right kidney weights, respectively, at the same timepoint. The mice with CSF-1 treatment were also found to have a 29% increase in the number of kidney glomeruli compared to age-matched litter mate control mice treated with phosphate buffered saline (FIG. 3). This demonstrates that CSF-1 can promote increased nephrogenesis that is associated with increased kidney growth.

Figure 4:
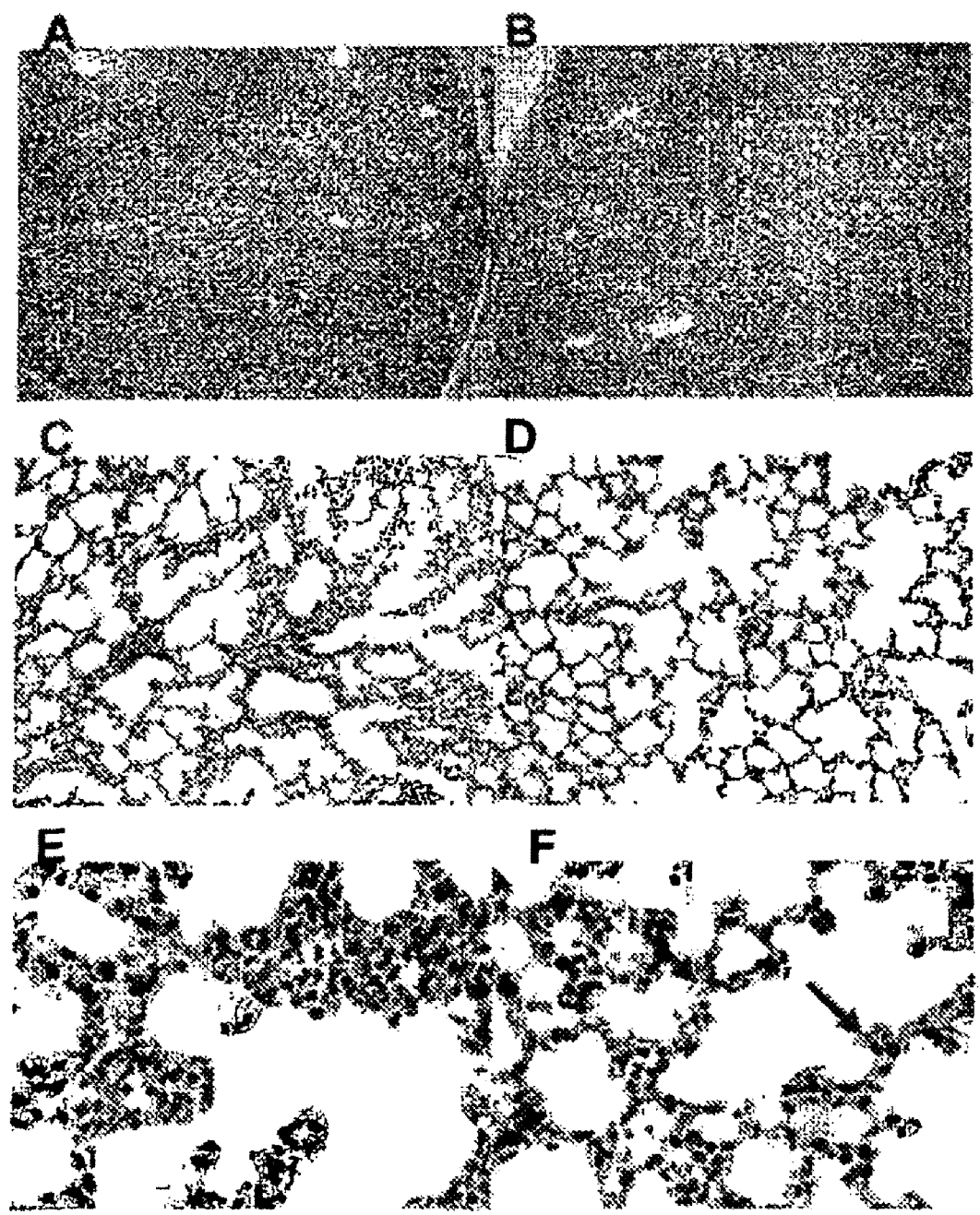
FIG. 4 shows the histology of kidneys from control (A; Mag ×100) and CSF-1 treated mice (B; Mag ×100) killed at day 29 and stained with haematoxylin and eosin; and the histology of lungs of control (C; Mag ×200, E; Mag ×400) and CSF-1-treated (D; Mag ×200, F; Mag ×400) mice.

FIG. 4 demonstrates the histology of the kidneys and lungs from CSF-1 (FIG. 4B, D, F) and control-treated (FIG. 4A, C, E) mice at day 29. There were no obvious structural abnormalities observed in the kidneys from mice following CSF-1 injection compared to control animals. On the other hand, the lungs from CSF-1-treated mice appeared more developed; in particular, the alveolar wall appeared to be thinner and less cellular, and there was less connective tissue compared to litter mate control animals. This corresponds to a greater degree of alveolarisation in the CSF-1-treated animals.

In conclusion, CSF-1 was observed to have a growth promoting effect on total and individual kidney weights when administered systemically to newborn mice. This increase in kidney weight in the CSF-1 treated mice was associated with increased nephrogenesis. In addition, the lungs of the CSF-1 treated mice appeared more differentiated compared to control litter mate animals. Therefore, it is considered that CSF-1 shows considerable promise for the treatment of pregnant mothers at risk of premature delivery, as well as in the treatment of premature babies with the objective to promote growth and maturation of the lungs and kidneys to prevent associated complications and disorders.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context to the disclosed embodiments. It is not to be taken as an admission that any or all of these matters form part of the prior art base or were common general knowledge in the field relevant to the present inventions as it existed in Australia or elsewhere before the priority date of each claim of this application.

It will be appreciated by persons skilled in the art that numerous variations and/or modifications may be made to the disclosed embodiments as shown herein without departing from the spirit or scope of the inventions as disclosed. The present embodiments are, therefore, to be considered in all respects as illustrative and not restrictive.

What is claimed is:

1. A method of promoting kidney development in a warm blood animal in need thereof, comprising:
   administering to the warm blooded animal a pharmaceutical composition comprising 0.1-1 g/kg body weight concentration of at least one kidney-development promoting component comprising:
   i) colony stimulating factor-1 protein (CSF-1);
   ii) a precursor of CSF-1;
   iii) a variant of CSF-1, comprising an isoform of CSF-1;
   iv) an analogue of CSF-1 having retained substantial similarity in biological function to CSF-1; or
   v) a derivative of CSF-1 having retained substantial similarity in biological function to CSF-1;
   wherein:
   a) the precursor, variant, analogue, or derivative of CSF-1 comprise the C-terminal fragment of CSF-1, comprising the C-terminal 150 amino acids of the 536 amino acid CSF-1 protein; and
   b) the promoted kidney development comprises one or more of the following: an increase in kidney weight, an increase in kidney growth, kidney maturation, increased nephrogenesis, or enhanced nephrogenesis.

2. The method of claim 1, wherein the CSF-1 is a bacterially-expressed, non-glycosylated recombinant CSF-1.

3. The method of claim 1, wherein the CSF-1 precursor, CSF-1 variant, CSF-1 analogue, and/or CSF-1 derivative comprises at least one of:
  i) at least 95% homology with CSF-1;
  ii) a conservative amino acid substitution;
  iii) a mature domain of CSF-1; or
  iv) a biologically-active fragment of CSF-1.

4. The method of claim 1, wherein the CSF-1 analogue and/or CSF-1 derivative comprises:
  i) a peptido-mimetic of CSF-1; or
  ii) a chemically modified, biologically-active fragment of CSF-1, comprising:
    a) pegylation;
    b) acylation; or
    c) linkage to a carrier, comprising human serum albumin or a histidine tag.

5. The method of claim 1, wherein the administered pharmaceutical composition is a nebulizable or injectable composition.

6. The method of claim 1, wherein the administered pharmaceutical composition is administered continuously for 8 hours over 1-7 consecutive days.

7. The method of claim 1, wherein the administered pharmaceutical composition is delivered at a rate of 0.01-1000 mg/hr.

8. The method of claim 1, wherein said warm blooded animal comprises a premature infant, a low birth weight infant, a foetus, a human, a pig, a horse, a dog, or other livestock.

9. The method of claim 8, wherein said warm blooded animal has low birth weight.

10. The method of claim 9, wherein colony stimulating factor-1 protein (CSF-1) is administered to said warm blooded animal.

11. The method of claim 10, wherein the pharmaceutical composition is administered systemically or locally.

12. The method of claim 11, wherein the pharmaceutical composition further comprises one or more of a pharmaceutically acceptable excipient, surfactant, vehicle, or diluents.

13. The method of claim 8, wherein said warm blooded animal has an underdeveloped kidney.

14. The method of claim 13, wherein colony stimulating factor-1 protein (CSF-1) is administered to said warm blooded animal.

15. The method of claim 14, wherein the pharmaceutical composition is administered systemically or locally.

16. The method of claim 15, wherein the pharmaceutical composition further comprises one or more of a pharmaceutically acceptable excipient, surfactant, vehicle, or diluents.

17. The method of claim 8, wherein said warm blooded animal is treated for complications arising from or related to low birth weight.

18. The method of claim 17, wherein colony stimulating factor-1 protein (CSF-1) is administered to said warm blooded animal.

19. The method of claim 18, wherein the pharmaceutical composition is administered systemically or locally.

20. The method of claim 19, wherein the pharmaceutical composition further comprises one or more of a pharmaceutically acceptable excipient, surfactant, vehicle, or diluents.

* * * * *